United States Patent [19]

Knidlberger

[11] Patent Number: 5,968,925
[45] Date of Patent: Oct. 19, 1999

[54] PROCESS FOR CONTINUOUS SINTERING OF GRANULES

[75] Inventor: Astrid Knidlberger, Holzkirchen, Germany

[73] Assignee: Boeters & Bauer, Germany

[21] Appl. No.: 08/983,598

[22] PCT Filed: May 21, 1996

[86] PCT No.: PCT/EP96/02177

§ 371 Date: Dec. 23, 1997

§ 102(e) Date: Dec. 23, 1997

[87] PCT Pub. No.: WO97/00673

PCT Pub. Date: Jan. 9, 1997

[30] Foreign Application Priority Data

Jun. 23, 1995 [DE] Germany .............. 195 22 899

[51] Int. Cl.$^6$ .................................................. A61K 31/55
[52] U.S. Cl. .................. 514/211; 514/567; 424/400; 424/451; 424/464
[58] Field of Search ...................... 424/400, 451, 424/464; 514/567, 211

[56] References Cited

U.S. PATENT DOCUMENTS 4,483,847 11/1984 Augart .

FOREIGN PATENT DOCUMENTS

WO 93/24110 12/1993 WIPO .
WO 95/09044 4/1995 WIPO .
PCT/EP96/ 02177 11/1996 WIPO .

*Primary Examiner*—Keith D. MacMillan
*Attorney, Agent, or Firm*—Brooks & Kushman P.C.

[57] ABSTRACT

The invention relates to a process for continuous sintering of granules for the preparation of pellets, in particular medicament formulations in tablet form.

17 Claims, No Drawings

PROCESS FOR CONTINUOUS SINTERING OF GRANULES

This application is a 371 of PCT/EP96/02177 filed May 21, 1996.

EP-B-0 043 254 describes a process for the preparation of medicament formulations with a delayed release of the active compounds which is based on a selective melting process on at least two lipid or lipoid components which have a retarding action for medicament active compounds mixed with these components. In these known processes, (a) the active compound is finely divided, (b) the finely divided active compound is mixed both with a finely divided high-melting lipid or lipoid component and with a finely divided low-melting lipid or lipoid component, the weight ratio of the two lipid or lipoid components being in the range from 1:5 to 5:1, (c) the resulting mixture of active compound and lipid or lipoid components is brought to a temperature which is above the melting point of the low-melting component but below the melting point of the high-melting component, the active compound and the high-melting lipid or lipoid component being dispersed uniformly in the completely molten low-melting lipid or lipoid component, (d) after melting of the low-melting component, the resulting mixture is cooled to below the melting point thereof and (e) the resulting mixture is granulated during cooling or thereafter.

WO-A-93/24110 describes a process for the preparation of sustained release medicament formulations in which the individual components (i) are extruded as partly molten product through a die plate with the aid of an extruder, (ii) the extrudate is cooled in the form of strands and (iii) fed to a granulator and (iv) the finished granules are subjected to tabletting.

However, according to EP-B-0 043 254, if the low-melting lipid or lipoid component is melted completely, modifications of these components or fat modifications can form, which can convert back later during storage of tablets which have been prepared using the known granules, such that the release of the active compound is influenced. In the process known from WO-A-93/24110, shearing effects can in turn occur, which can lead to abrasion of material in the extruder tube or on the die plate and therefore to an undesirable introduction of metal into the extrudate.

The object of the present invention is to improve the prior art described.

For this purpose, according to the invention, a process is provided for continuous sintering of granules for the preparation of pellets, in particular medicament formulations in the form of tablets, in which (a) the individual components are mixed to form a powder, (b) the powder obtained is introduced in the dry state into an extruder, (c) the powder introduced is conveyed with the aid of a conveying screw in the direction of the open extruder front or the ejector, (d) the extruder and/or the screw being heated and one or some of the components being made into a paste or softening (at any rate none of the components melting) and particles of the powder mixture sticking together or sintering to form granules, (e) if appropriate, the sintered granules obtained are sieved and (f) tabletting is carried out in a manner known per se.

The process claimed thus operates under normal pressure, since a die is lacking. The occurrence of shearing forces, as in known extrusion, is largely avoided in this way, so that there is practically no abrasion of the extruder tube or on a die provided in the prior art, and therefore no introduction of metal occurs. Since no single one of the components employed is melted, and since also no strand is extruded, the material emerging from the extruder in the process according to the invention is obtained as granules, so that it does not have to be subjected to a separate granulating stage. Instead, the material emerging from the extruder can be sieved, if necessary, the sieve residue being fed to tablet making, while the material which passes through the sieve can be fed into the process according to the invention again.

A lipid or lipoid component can be used as one of the components for the powder introduced into the extruder.

Components which include an active compound which has a water-solubility of greater than 0.5% can be used as starting substances in the process according to the invention. Examples of active compounds are Diltiazem, Sotalol, Diclofenac or one of their derivatives, such as Diltiazem.HCl, Sotalol.HCl or Diclofenac sodium.

In the process according to the invention, the extruder and/or the screw can be heated in zones, three or more zones following one another (in the conveying direction), the middle zone(s) of which has (have) a higher temperature than the flanking zones.

According to the invention, a screw in which (in the conveying direction), a zone of given thread width and thread pitch is followed by a zone of greater thread width and/or flatter thread pitch. The zones of different thread width and/or thread pitch can be provided here, for example, with the aid of individual elements of the screw connected to one another.

According to the invention, two combing screw bodies arranged parallel to one another and running in the same direction or opposite directions can also be provided as the screw.

The invention is illustrated in more detail by examples below.

EXAMPLE 1

(Diltiazem 90 mg Sustained Release Tablet)

The components of the inner phase were sieved, if necessary, weighed and mixed. The procedure was analogous for the components of the outer phase. The following recipes were chosen here.

| | | |
|---|---|---|
| Inner phase | Diltiazem.HCl | 90.00 |
| | Cutina HR | 100.00 |
| | Lactose | 30.00 |
| | Polyvidone | 20.00 |
| | PEG | 20.00 |
| Outer phase | Microcrystalline cellulose | 62.00 |
| | Na carboxymethyl-starch | 1.70 |
| | Highly disperse silicon dioxide | 3.30 |
| | Magnesium stearate | 3.00 |
| Total: | | 330.00 |

The mixture of the inner phase was introduced into the reservoir tank of an extruder. The extruder was operated without a breaker plate, so that no pressure built up in the extruder barrel. In the extruder used, four temperature zones followed one another in the conveying direction as follows:

| Zone 1 | Zone 2 | Zone 3 | Zone 4 |
|---|---|---|---|
| 42 ± 5° C. | 68 ± 5° C. | 72 ± 5° C. | 57 ± 5° C. |

The individual zones were heated up to the stated temperatures, the mixture for the inner phase being passed through the extruder after the stated temperatures had been reached. Granules which could be sieved and were mixed with the mixture for the outer phase were obtained at the discharge. This mixture was pressed to tablets.

EXAMPLE 2
(Diltiazem 120 mg Sustained Release Tablet)

The procedure was as in Example 1, but the following recipes were provided for the inner phase and the outer phase and the following temperatures were provided for the four successive temperature zones.

| Inner phase | Diltiazem.HCl | 120.00 |
|---|---|---|
| | Cutina HR | 46.00 |
| | Lactose | 208.00 |
| | Stearic acid | 70.00 |
| Outer phase | Hydroxyethylcellulose | 3.20 |
| | Magnesium stearate | 1.50 |
| Total: | | 448.70 |

| Zone 1 | Zone 2 | Zone 3 | Zone 4 |
|---|---|---|---|
| 44 ± 5° C. | 69 ± 5° C. | 70 ± 5° C. | 52 ± 5° C. |

EXAMPLE 3
(Sotalol 240 mg Sustained Release Tablet)

Example 1 was followed, but a 2-layered tablet was prepared with the following recipes and the following temperatures were provided for the successive temperature zones.

| Initial layer | Sotalol.HCl | 40.00 |
|---|---|---|
| | Lactose | 30.00 |
| | Maize starch | 30.00 |
| | Hydroxypropylcellulose | 3.00 |
| | Blue lacquer | 0.12 |
| | Purified water q.s. | 15.0 |
| | Na carboxymethyl-starch Lactose | 35.00 |
| | Highly disperse silicon dioxide | 1.0 |
| | Magnesium stearate | 2.0 |
| Total: | | 156.12 |
| Sustained release layer | | |
| Inner phase | Sotalol.HCl | 200.0 |
| | Lactose | 100.0 |
| | Cutina HR | 140.0 |
| Outer phase | Magnesium stearate | 4.0 |
| Total | | 446.0 |

| Zone 1 | Zone 2 | Zone 3 | Zone 4 |
|---|---|---|---|
| 50 ± 5° C. | 71 ± 5° C. | 69 ± 5° C. | 49 ± 5° C. |

EXAMPLE 4
(Diclofenac 100 mg Sustained Release Tablet)

Example 1 was followed, but the following recipes were provided for the inner phase and the outer phase and the following temperatures were provided for the four successive temperature zones.

| Inner phase | Diclofenac sodium | 100.00 |
|---|---|---|
| | Sucrose | 105.00 |
| | 1-Hexadecanol | 55.20 |
| Outer phase | Highly disperse silicon dioxide | 0.52 |
| | Magnesium stearate | 1.30 |
| | Poly-(1-vinyl-2-pyrrolidone) | 1.28 |

| Zone 1 | Zone 2 | Zone 3 | Zone 4 |
|---|---|---|---|
| 50 ± 5° C. | 64 ± 5° C. | 63 ± 5° C. | 48 ± 5° C. |

I claim:
1. A process for continuous sintering of granules for the preparation of pellets, comprising:
   (a) mixing the individual components to form a powder;
   (b) introducing the powder obtained in step (a) in the dry state into an extruder;
   (c) conveying said powder with the aid of a conveying screw in the direction of the open extruder front;
   (d) heating one or both of the extruder or the screw, one or more of the components of the powder mixture softening or melting, thereby sintering particles of the powder mixture together to form granules; and
   (e) optionally sieving said granules.

2. A process according to claim 1, wherein a lipid or lipoid component is used as one of the components for the powder.

3. A process according to claim 1, wherein a pharmaceutically active component having a water-solubility of >0.5% is used as a starting substance.

4. A process according to claim 2, wherein a pharmaceutically active component having a water-solubility of >0.5% is used as a starting substance.

5. A process according to claim 1, wherein Diltiazem, Sotalol, Diclofenac or a derivative thereof is employed as a portion of said powder.

6. A process according to claim 2, wherein Diltiazem, Sotalol, Diclofenac or a derivative thereof is employed as a portion of said powder.

7. A process according to claim 1, wherein one or both of said extruder or said screw is heated in zones, three or more zones following one another in the conveying direction, the middle zone(s) of which has (have) a higher temperature than the flanking zones.

8. A process according to claim 2, wherein one or both of said extruder or said screw is heated in zones, three or more zones following one another in the conveying direction, the middle zone(s) of which has (have) a higher temperature than the flanking zones.

9. A process according to claim 3, wherein one or both of said extruder or said screw is heated in zones, three or more zones following one another in the conveying direction, the middle zone(s) of which has (have) a higher temperature than the flanking zones.

10. A process according to claim 5, wherein one or both of said extruder or said screw is heated in zones, three or more zones following one another in the conveying direction, the middle zone(s) of which has (have) a higher temperature than the flanking zones.

11. A process according to claim 1, wherein a screw in which, in the conveying direction, a zone of given thread width and thread pitch is followed by a zone having one or both of a higher thread width or flatter thread pitch is employed as said screw.

12. A process according to claim 2, wherein a screw in which, in the conveying direction, a zone of given thread width and thread pitch is followed by a zone having one or both of a higher thread width or flatter thread pitch is employed as said screw.

13. A process according to claim 3, wherein a screw in which, in the conveying direction, a zone of given thread width and thread pitch is followed by a zone having one or both of a higher thread width or flatter thread pitch is employed as said screw.

14. A process according to claim 5, wherein a screw in which, in the conveying direction, a zone of given thread width and thread pitch is followed by a zone having one or both of a higher thread width or flatter thread pitch is employed as said screw.

15. A process according to claim 14, wherein the zones of different thread width or thread pitch are provided with the aid of individual elements of the screw connected to one another.

16. The process of claim 1 wherein said extruder contains two corotating or counterrotating parallel screws.

17. A process for preparing a pharmaceutical tablet comprising preparing a sintered granulate by the process of claim 1 and compressing said granulate to form a tablet.

* * * * *